US011650265B2

(12) United States Patent
White (10) Patent No.: US 11,650,265 B2
(45) Date of Patent: May 16, 2023

(54) ELECTRIC METER HAVING GAS SENSOR FOR ARC DETECTION

(71) Applicant: Honeywell International Inc., Morris Plains, NJ (US)

(72) Inventor: Aleksandr Douglas White, Raleigh, NC (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 82 days.

(21) Appl. No.: 17/191,384

(22) Filed: Mar. 3, 2021

(65) Prior Publication Data

US 2022/0283245 A1 Sep. 8, 2022

(51) Int. Cl.
*G01R 31/52* (2020.01)
*G01R 31/40* (2020.01)
*G08B 21/12* (2006.01)
*G08B 21/18* (2006.01)
*G01N 33/00* (2006.01)

(52) U.S. Cl.
CPC .............. *G01R 31/52* (2020.01); *G01R 31/40* (2013.01); *G08B 21/12* (2013.01); *G08B 21/182* (2013.01); *G01N 33/0037* (2013.01); *G01N 33/0039* (2013.01)

(58) Field of Classification Search
CPC ........ G01R 31/52; G01R 31/40; G08B 21/12; G08B 21/182; G01N 33/0037; G01N 33/0039
See application file for complete search history.

(56) References Cited

U.S. PATENT DOCUMENTS

| 7,513,683 | B2 | 4/2009 | Sanderford et al. |
| 8,304,676 | B2 | 11/2012 | Uchii et al. |
| 9,594,107 | B1 * | 3/2017 | Lawton ............. G01R 31/1227 |
| 10,511,157 | B2 | 12/2019 | Whitehouse et al. |
| 2001/0054552 | A1 * | 12/2001 | Matsuo ................ G01N 27/407 |
| | | | 204/422 |

(Continued)

OTHER PUBLICATIONS

Dutta, S., et al., "Preventing Electric Meter Fires: Two Perspectives," Powergrid International, Dec. 15, 2014, 9 pages, vol. 19, Issue No. 12, Powergrid International, USA.

*Primary Examiner* — Christopher P McAndrew
*Assistant Examiner* — Zannatul Ferdous
(74) *Attorney, Agent, or Firm* — John Maldjian; Stevens & Lee PC (57) ABSTRACT

An electric meter includes a meter shell configured to be within an outer utility box. A meter socket and blades are for coupling to openings of the socket. The openings include utility-side and premises-side openings for the blades to extend into. A meter processor is coupled to measurement circuitry, and to a communications unit including a transceiver. A gas sensor is positioned proximate to the blades for sensing ≥1 gaseous compound product resulting from an arc discharge across air involving the blades. During operation of the electric meter, responsive sensing a presence of the gaseous compound product, the gas sensor generates an output signal. Responsive to the output signal being above a predetermined threshold level, the electric meter triggers an alert signal that is transmitted to an advanced metering infrastructure (AMI) which indicates an identity of the electric meter and that the electric meter had experienced the arc discharge.

13 Claims, 5 Drawing Sheets

(56) References Cited

U.S. PATENT DOCUMENTS

| | | | |
|---|---|---|---|
| 2008/0022754 A1* | 1/2008 | Nakagawa | G01N 27/4077 73/31.05 |
| 2009/0071231 A1* | 3/2009 | Fujii | G01N 27/4077 73/31.05 |
| 2020/0103318 A1* | 4/2020 | Yang | F04B 43/046 |
| 2021/0088573 A1* | 3/2021 | Ferraro | G01R 31/1272 |
| 2022/0050081 A1* | 2/2022 | Seo | G01N 29/32 |

* cited by examiner

ELECTRIC METER HAVING GAS SENSOR FOR ARC DETECTION

FIELD

Disclosed aspects relate to electrical utility systems, and more specifically to detecting electrical arcs between electrical metering components of electric meters.

BACKGROUND

An electric arc, or an arc discharge referred to herein as simply an "arc", involves an electrical breakdown of at least one type of molecule of an ionizable gas that results in a prolonged electrical discharge in the form of electrical current flowing between two electrically conductive points known as electrodes. The electrodes are at different electrical potentials (or voltages) which are separated from one another by the ionizable gas or a gas mixture including the ionizable gas. The current through a normally non-electrically conductive medium such as air (which is known to be a mixture of gas being primarily comprising nitrogen as a diatomic $N_2$) produces a plasma, where the plasma may produce a visible light emission. The current due to an arc flows between electrodes referred to as a cathode and an anode. The term arc refers both to the device itself as well as to the electric discharge that takes place within the device. Arcs can occur under conditions of high pressure, atmospheric pressure, or below atmospheric pressure, and can utilize a variety of gases or gas mixtures.

Regarding the electrical conductivity of gases, gases are normally poor conductors of electricity. The atoms or molecules of gases usually contain no free electrons needed for an electrical current to flow. That condition can change, however. If sufficient energy is supplied to the gas, its atoms or molecules can break apart (ionize) into charged particles. For example, if a spark is passed through a container of oxygen gas ($O_2$), the $O_2$ molecules ionize to form some positively charged oxygen ions as well as and some negatively charged oxygen ions. These charged particles then make it possible for the gas to become electrically conductive.

An arc can cause a fire once the electrical energy from the arc is converted into thermal energy (heat) which through heat transfer to a combustible material can result in ignition that initiates and sustains the fire. Various types of damage, wear, improper installation, or other faults, may cause arcing between two adjacent conductors, or between the ends of two parts of a broken or weakened conductor, or across a loose electrical connection.

Residential and commercial premises generally include electric meters to allow the electric utility company to monitor the consumption of electricity on the premises. An electric meter generally includes an outer utility box, and includes a meter socket having openings (sometimes referred to as jaws) configured for receiving blades, where the utility box is generally positioned on an outside wall of the premises. Inside the utility box is a meter shell having therein a meter portion generally implemented on a printed circuit board (PCB)) including measurement circuitry, where the metering circuitry is for measuring the consumption of electricity, and generally also a communications unit comprising a radio component comprising a transmitter configured to communicate the electricity consumption measurements to the central system of the utility company for billing and for other purposes. The premises-side of the electric meter is electrically connected by some blades to what may be considered premises-side openings of the meter socket, and there also blades for connecting power lines from the electric utility company to what may be considered utility-side openings of the meter socket.

SUMMARY

This Summary is provided to introduce a brief selection of disclosed concepts in a simplified form that are further described below in the Detailed Description including the drawings provided. This Summary is not intended to limit the claimed subject matter's scope.

Disclosed aspects recognize the problem of automatically and promptly detecting an arc in the meter socket of an electric meter which is also known as hot sockets. When pulling a significant electrical load on one of the electrical phases (such as due to supplying power to an air conditioning (AC) unit), the electric meter can become hot, and one may be able to hear arcing, and the lights in the premises may also flicker. A loose meter socket connection can cause one or more blades to become open "contacts" that have high resistance which can cause overheating and loss of tension so the electric meter is no longer making a good (low resistance) connection to its meter socket, which once detected can generally be resolved by retightening the contacts.

The heat resulting from an arc can create sufficient heat to in some cases where there is an adjacent flammable material to lead to a fire at the premises, thus presenting a significant financial risk for electric utility companies. The ability to automatically and promptly detect and then mitigate an arc by identifying arcing at an early stage makes it possible to take prompt corrective action such as retightening contacts, or in a severe arcing case disconnecting the electric meter, and also replacing the meter socket, which provides value to electric utility companies as well as to the end-user customers at the premises.

One disclosed aspect comprises an electric meter includes a meter shell configured to be within an outer utility box. A meter socket and blades are for electrically coupling to openings of the socket, the openings including utility-side openings and premises-side openings, wherein the blades are configured to extend into the openings. A meter processor is coupled to measurement circuitry, and to a communications unit including a transceiver. A gas sensor is positioned in a location proximate to the blades for sensing at least one gaseous compound product resulting from an arc discharge across the air involving the blades. During operation of the electric meter, responsive to the gas sensor sensing a presence of the gaseous compound product, the gas sensor generates an output signal. Responsive to the output signal being determined to be above a predetermined threshold level, the electric meter triggers an alert signal that is transmitted to an advanced metering infrastructure (AMI), where the alert signal indicates an identity of the electric meter and that the electric meter had experienced the arc discharge.

DETAILED DESCRIPTION

Disclosed aspects are described with reference to the attached figures, wherein like reference numerals are used throughout the figures to designate similar or equivalent elements. The figures are not drawn to scale and they are provided merely to illustrate certain disclosed aspects. Several disclosed aspects are described below with reference to example applications for illustration. It should be understood that numerous specific details, relationships, and methods are set forth to provide a full understanding of the disclosed aspects.

It is recognized herein that by volume, dry air contains about 78.09% nitrogen ($N_2$), 20.95% oxygen ($O_2$), 0.93% argon, 0.04% carbon dioxide, and small amounts of other gases. Air also contains a variable amount of water vapor, on average around 1% when at sea level, and 0.4% over the entire atmosphere. This gas mixture in air upon being in the path of an electrical arc for an electric meter, such as between blades and openings of a meter socket, can form gaseous compound molecules including NO, $NO_2$, and $O_3$.

Figure 1:
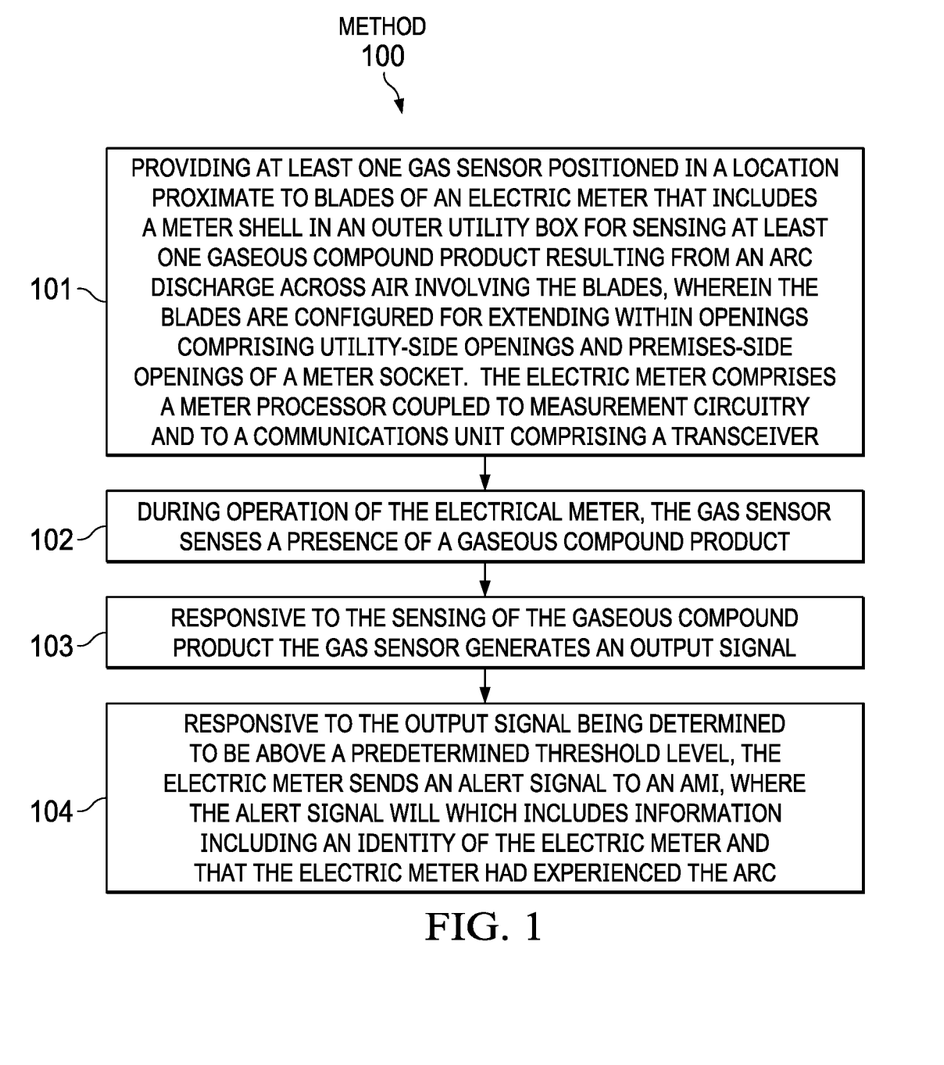
FIG. 1 is a flow chart that shows steps in a method of detecting arcs in air generated by an electric meter using at least one gas sensor configured to detect at least one gaseous compound product resulting from the arc, according to an example aspect.

FIG. 1 is a flow chart that shows steps in a method 100 of detecting arcs generated in air by an electric meter using at least one gas sensor positioned in proximity to at least one of the blades of electric meter, where the gas sensor is configured to detect at least one gaseous compound product resulting from the arc, according to an example aspect. The gas sensor can be located internally relative to the meter shell generally positioned (soldered onto) on the PCB pf the meter portion of the electric meter, where there are ventilation holes in the meter shell (See electric meter 202 in FIG. 2A described below). Alternatively, the gas sensor can be positioned externally relative to the meter shell, generally on the face of meter shell that the blades protrude-from the electric meter (See electric meter 252 in FIG. 2B described below). In either arrangement the gas sensor is connected for receiving electrical power and sending its output signal to the meter processor.

Regarding gas sensor proximity to the blades, as used herein this means a maximum of 2 inches (equal to 5.08 cm) away from a closest blade. In the case the gas sensor(s) is internally positioned behind the front wall which the blades extrude from there is generally some ventilation openings (see the vent hole 271 in FIG. 2A described below) through the meter shell to enable the gaseous compound molecule(s) to be detected by the gas detector. Proximity thus allows gas meter placement on sides of the meter shell or on the PCB for the meter portion, or also within a cavity that is not on or behind the front wall. There can be 2 or more gas sensors to enable detecting different gases such as NO and $NO_2$, or the same gas sensor type for providing redundancy, at one or more of these proximate locations.

Step 101 comprises providing at least one gas sensor positioned in a location proximate to blades of an electric meter that includes an outer utility box for sensing at least one gaseous compound product resulting from an arc discharge across air involving the blades, where the blades are extending within openings comprising utility-side openings and premises-side openings of a meter socket. The electric meter has an outer meter shell and comprises a meter processor coupled to measurement circuitry and to a communications unit comprising a transceiver.

A gas sensor is known in the sensing arts to be a device which detects the presence and generally also the concentration of a gas in an atmosphere of interest. Based on the concentration of the gas being detected, the gas sensor can generate a corresponding potential difference by changing the resistance of the sensor material (such as a metal oxide) inside the gas sensor, which can be measured by the gas sensor reflected as an output voltage. Based on the measured output voltage value, the type and concentration of the gas can be estimated. The type of gas the gas sensor can detect is known to depend on the sensing material present inside the gas sensor. Generally, gas sensors are available as modules (or packages) together with comparators, where the comparators can be set for a particular threshold value of gas concentration. When the concentration of the gas exceeds this threshold, the digital pin of the sensor package generally goes high. The analog pin of the sensor package can be used as a measure the concentration of the gas. If it is desired to detect more than one gas generated by an arc discharge, there is generally needed a separate sensor for the sensing of each of nitric oxide (NO), nitrogen dioxide ($NO_2$) and ozone ($O_3$). However, sensing any one of these gases in a sufficient concentration is generally sufficient for detecting an arc.

The arc detected is generally between the blades and the openings of the meter socket that connect the load at the premises (metered site) to the power line of the main power grid of the electric utility. The electric meter is generally a smart electric meter, where the 'smart' feature refers to the electric meter having the features of recording therein information such as the consumption of electrical energy, voltage levels, current and power factor, and also includes a transceiver. Optionally, the electric meter can include hardware including an antenna coupled an output of the transceiver along with optional software for supporting the feature of wireless communications. Disclosed methods and electric meters generally seek to detect arcing between any of the blades (see blades 303 in FIG. 3A described below) and any of the openings (including utility-side openings 305a and a premises-side opening 305b also shown in FIG. 3A described below).

Step 102 comprises during operation of the electrical meter; the gas sensor senses a presence of a gaseous compound product. The gaseous compound product resulting from the arc across the air detected by the gas sensor as described above can comprise at least one of NO, $NO_2$, and $O_3$. One example gas sensor that can generally be used for a disclosed gas sensor in the case of detecting $NO_2$ is an electrochemical type sensor marketed by PEWATRON that is configured as a gas sensor module which has a selectable measurement range including 0 to 5 parts per million (ppm), 0 to 50 ppm, 0 to 100 ppm, or 0 to 1,000 ppm.

Step 103 comprises responsive to the sensing of the gaseous compound product the gas sensor generates an output signal. As noted above, the output signal is generally a voltage level, and the gas level (concentration) data from the gas sensor is generally a PPM reading. In step 104 described below, the gas level reading is flagged and acted on by sending to an alert signal to an advanced metering infrastructure (AMI) if a predetermined threshold level is exceeded. A comparator may be used to determine if the predetermined threshold level is exceeded, in which case the alert signal is sent to the AMI, which as described above can be provided by a gas sensor package. AMI is known to be a two-way communication system to collect detailed metering information throughout a utility's service industry. AMI is typically automated and allows real-time, on-demand interrogations with metering endpoints. The US federal energy regulatory commission (FERC) defines AMI as "A metering system that records customer consumption hourly or more frequently and that provides for daily or more frequent transmittal of measurements over a communication network to a central collection point."

Step 104 comprises responsive to the output signal being determined to be above a predetermined threshold level, the electric meter sends an alert signal to an AMI, where the alert signal will generally include information including an identity (for example the serial number, they can be a manufacturer assigned serial number or a utility assigned identifier) of the electric meter, and that the electric meter had experienced the arc. Optionally, the alert signal can also include an estimate of the severity of the arcing which can be determined by the gas level estimate provided by the gas sensor. The comparator for performing a level comparison can be implemented as a digital comparator or by an analog comparator, where the alert signal when generated when the level is determined to be sufficiently high relative to a predetermined threshold level to indicate an arc, is sent to the AMI.

The alert signal can be a wireless (radiofrequency (RF)) signal in the case that the electric meter has wireless communication capability including an antenna. Alternatively, the alert signal can be sent over the powerline itself as a powerline communication signal. Powerline communication (also known as power-line carrier or PLC) carries data on the same electrical conductor (powerline) that is also used at the same time for electric power transmission or electric power distribution to the premises being served by the electric utility. As noted above, when the alert signal is sent to an AMI, the alert signal can be sent to the electric utility's head end system also known as a central system, or to generally to any software comprising system that ingests events, readings, or metrics, from electric meters.

There are several examples approaches as to the uptime for the gas sensor. In first example approach, the sensor(s) is/are constantly read and profiled and minimum/maximum/ average readings are relayed to the central system of the electric utility at a selected interval frequency. In a second example approach, the sensor is 'woken' up from a sleep mode at an interval which can be time based, or can be triggered by external stimuli such as a light sensor or the internal meter circuitry detecting increased load. In a third example approach, the electric meter is constantly records readings from the sensor(s) at a high time resolution (seconds or sub-seconds). After the electric meter has the data, the data is sent to the AMI as it is recorded or alternatively in large batches of readings. It is noted although this would not generally be practical for traditional AMI networks, this data transfer is generally practical for newer AMI networks that use existing wireless and cellular networks.

Figure 2A:
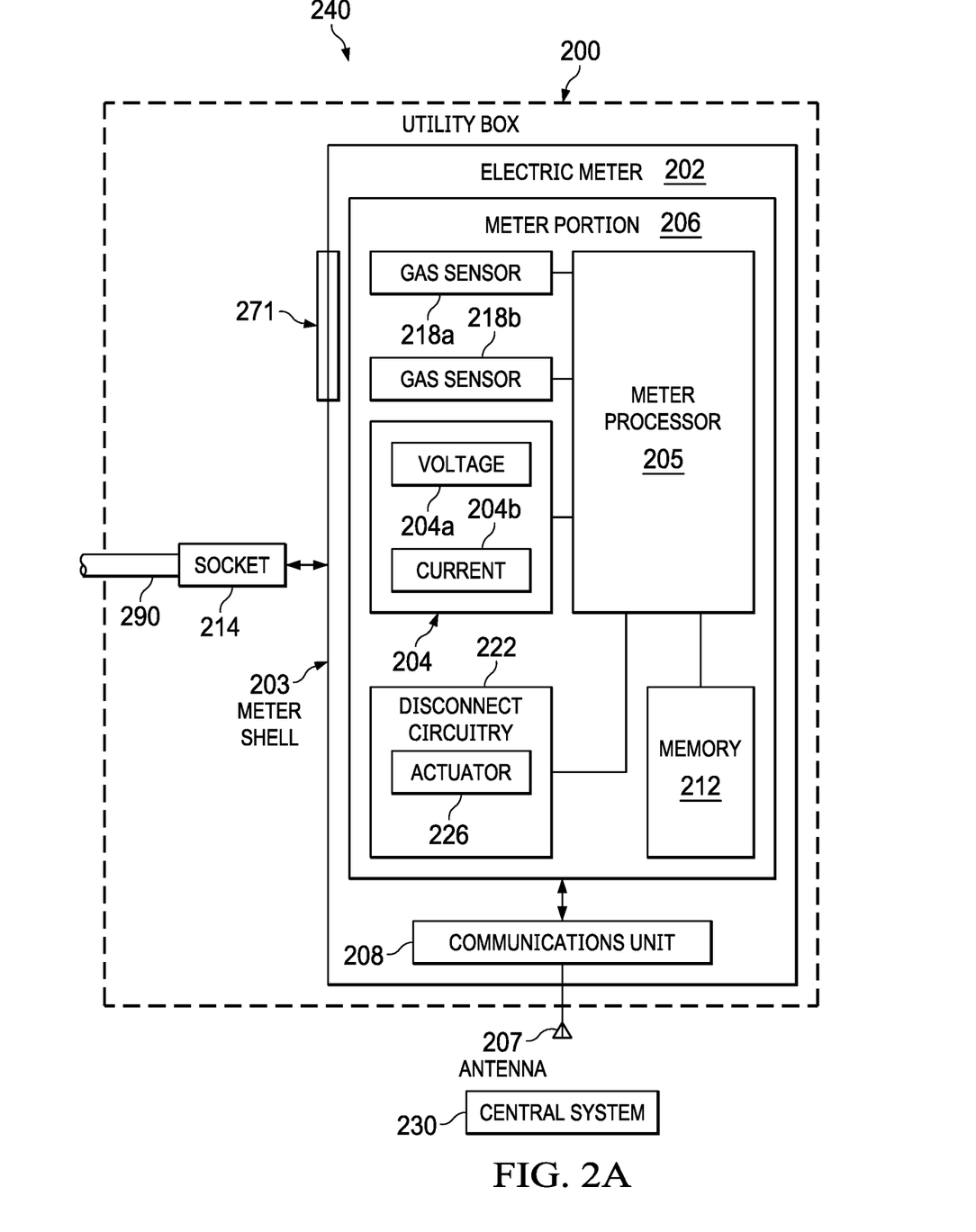
FIG. 2A is a block diagram system portion representation of a disclosed electric meter having a meter shell with a gas sensor positioned on the PCB of the meter portion, where there is at least one vent hole through the meter shell that facilitates the compounds generated by the arc to enter within the meter shell to enable such compounds to be sensed by the gas sensor, where the gas sensor is configured to implement a disclosed method of detecting arcs generated by a utility meter, according to an example aspect.

FIG. 2A is a block diagram system portion representation 240 of a disclosed electric meter 202 having a meter shell 203 having at least one gas sensor shown as a first gas sensor 218a and a second gas sensor 218b positioned on the PCB of the meter portion 206, where the electric meter 202 is configured to implement at a premises a disclosed method of detecting arcs when generated, according to an example aspect. There is at least one vent hole 271 through the meter shell 203 that facilitates the compounds generated by the arc to enter within the meter shell 203 to enable such compounds to be sensed by the gas sensors 218a, 218b.

There can be one, two, or three or more vent holes 271. As shown, the electric meter 202 comprises a meter portion 206 generally implemented on a PCB including measurement circuitry 204 including a voltage measurement circuit 204a and a current measurement circuit 204b for measuring the amount of electricity that is being consumed. The electric meter 202 also includes a meter processor 205 such as a microprocessor or other computing device that has an associated memory 212 which can act to run algorithms stored in the memory 212, and also can function as a controller to control the overall functions of the electric meter 202. The memory 212 is generally also for storing program instructions. Although not shown, a display is generally also included for displaying at least the meter data and status information.

The electric meter 202 besides the meter portion 206 comprises a communications unit 208 that can be a wireless communications unit, generally comprising a transceiver that is shown coupled to an antenna 207, for wirelessly transmitting and receiving data to/from other electric meters that may be equivalent to electric meter 202. The wireless communication unit 208 may comprise, for example, a CC1110Fx/CC1111fX semiconductor device available from Texas Instruments Incorporated® which comprises a Low-Power SoC (System-on-Chip) with MCU, memory, Sub-1 GHz RF Transceiver, and a USB controller.

Within the utility box 200 is also a meter socket 214 which is coupled between the other components of the electric meter 202 and the power lines shown as 290. The power lines 290 electrically connect to the meter socket 214 to supply power to a premises from the utility company. The electrical power received from the power lines 290 may be routed through the meter socket 214 to allow the blades of the electric meter 202 (see blades 303 in FIG. 3A described below) to be positioned in the openings of the meter socket 214 to monitor the power levels consumed within the premises.

The blades are generally sized to be positioned within openings of the meter socket 214. Positioning the blades of the electric meter 202 within the meter socket 214 electrically connects the electric meter 202 to the meter socket 214. The meter socket 214 may include springs or other features to provide a tension force on the blades to maintain the position of the blades within the opening of the meter socket 214. The meter socket 214 and blades may each include one or more surfaces made out of an electrically conductive material to allow electricity to flow between the meter socket 214 and the blades.

The measurement circuitry 204 using its voltage sense circuit 204a and current sense circuit 204b measures the power consumed by the premises from the electrical signals supplied to the premises through the power lines 290. The voltage sense circuit 204a may be connected to electric load terminals in the electric meter 202, which are connected to the meter socket 214 using the blades of the electric meter 202.

The voltage sense circuit 204a generally includes amplifiers, resistors, or other electrical devices to generate a voltage sense signal corresponding to an instantaneous voltage from the power lines. The current sense circuit 204b may include, for example transformers, inductors, or other coils connected to the meter socket 214 via the blades of the meter system 202 to generate a current sense signal corresponding to an instantaneous current flowing from the power lines 290 through the meter socket 214. Voltage sense signals and current sense signals generated by the voltage sense circuit 204a and the current sense circuit 204b can be routed to the meter processor 205 for monitoring the signals and determining the power consumed by the premises. Based on one or more of the voltage sense signals and current sense signals, measurements may be generated by the meter processor 205.

The meter processor 205 may comprise one or more processors communicatively coupled to the memory device 212. The meter processor 205 is configured to execute instructions stored by the memory device 212, and for example includes a logical processing unit, a microprocessor, a digital signal processor, or another processing for processing the signals received from the voltage sense circuit 204a and the current sense circuit 204b. The memory device 212 device can include includes volatile or non-volatile random access memory (RAM), electrically erasable programmable read-only memory (EEPROM), or other readable and writeable memory devices. For example, the memory device 212 may include a non-volatile memory that stores data representing the measurements received from the voltage sense circuit 204a and the current sense circuit 204b.

The meter portion 206 also optionally includes disconnect circuitry 222 which is a conventional feature provided by most commercially available smart electric meters. During operation, a system, such as the central system on the AMI, responsive to the alert signal sent by the electric meter will send a signal to the electric meter commanding the disconnect circuitry 222 to implement a disconnection. In some aspects, the disconnect circuitry 222 includes a switching device or other circuitry for disconnecting the power supplied from the power lines 290 to the premises through the meter socket 214. Disconnecting the power may include interrupting electrical signals that are transmitted between the meter socket 214 and the electric meter 202.

The disconnect circuitry 222 may also include an actuator 226 coupled to the switching device. The actuator 226 may cause the switching device of the disconnect circuitry 222 to transition from a first position that allows power to flow into the premises to a second position that prevents the power from flowing into the premises, and from the second position to the first position. The actuator 226 may be communicatively coupled to the meter processor 205, which can transmit control signals to the disconnect circuitry 222 to allow the meter processor 205 to operate the switching device.

The communications unit 206 through its associated antenna 207 is shown communicatively coupled to a central system 230, such as a central system associated with an operator of the power utility. In some disclosed aspects, the communication unit 206 may transmit an alert signal indicating an arc associated with the utility box 200.

In the case the electric meter 202 comprises a smart meter, this enables enable two-way communication between the electric meter 202 and an AMI shown as the central system 230. AMI differs from automatic meter reading (AMR) in that it enables two-way communication between the electric meter and the electric utility. Communications from the electric meter to the network as noted above may be wireless, or via a fixed wired connections such as PLC. Wireless communication options include cellular communications, Wi-Fi (readily available), wireless ad hoc networks over Wi-Fi, wireless mesh networks, low power long-range wireless (LoRa), ZigBee (low power, low data rate wireless), and Wi-SUN (Smart Utility Networks).

Figure 2B:
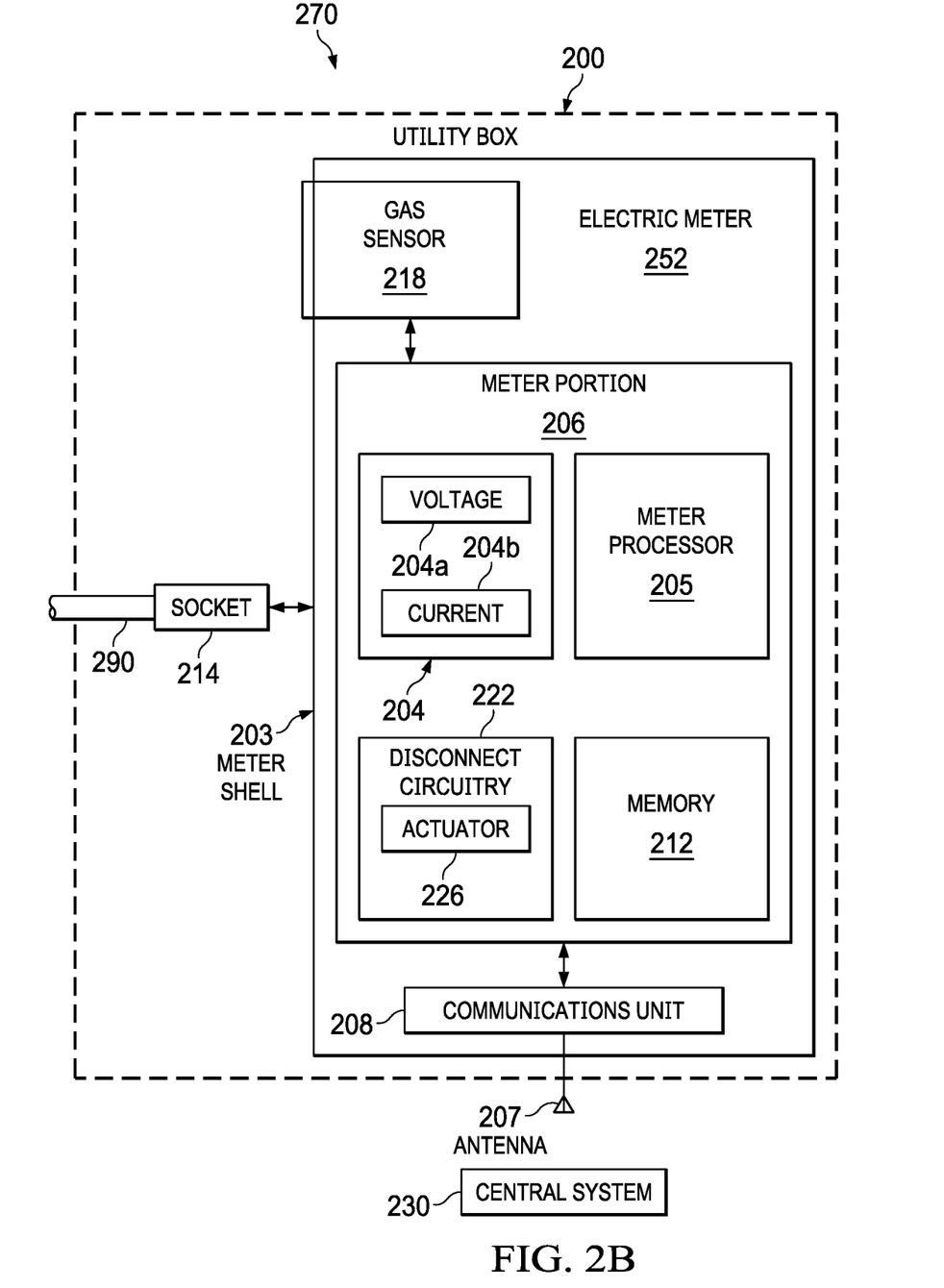
FIG. 2B is a block diagram system portion representation of a disclosed electric meter having at least one gas sensor that is configured to implement a disclosed method of detecting arcs generated by an electric meter, according to an example aspect.
Figure 3A:
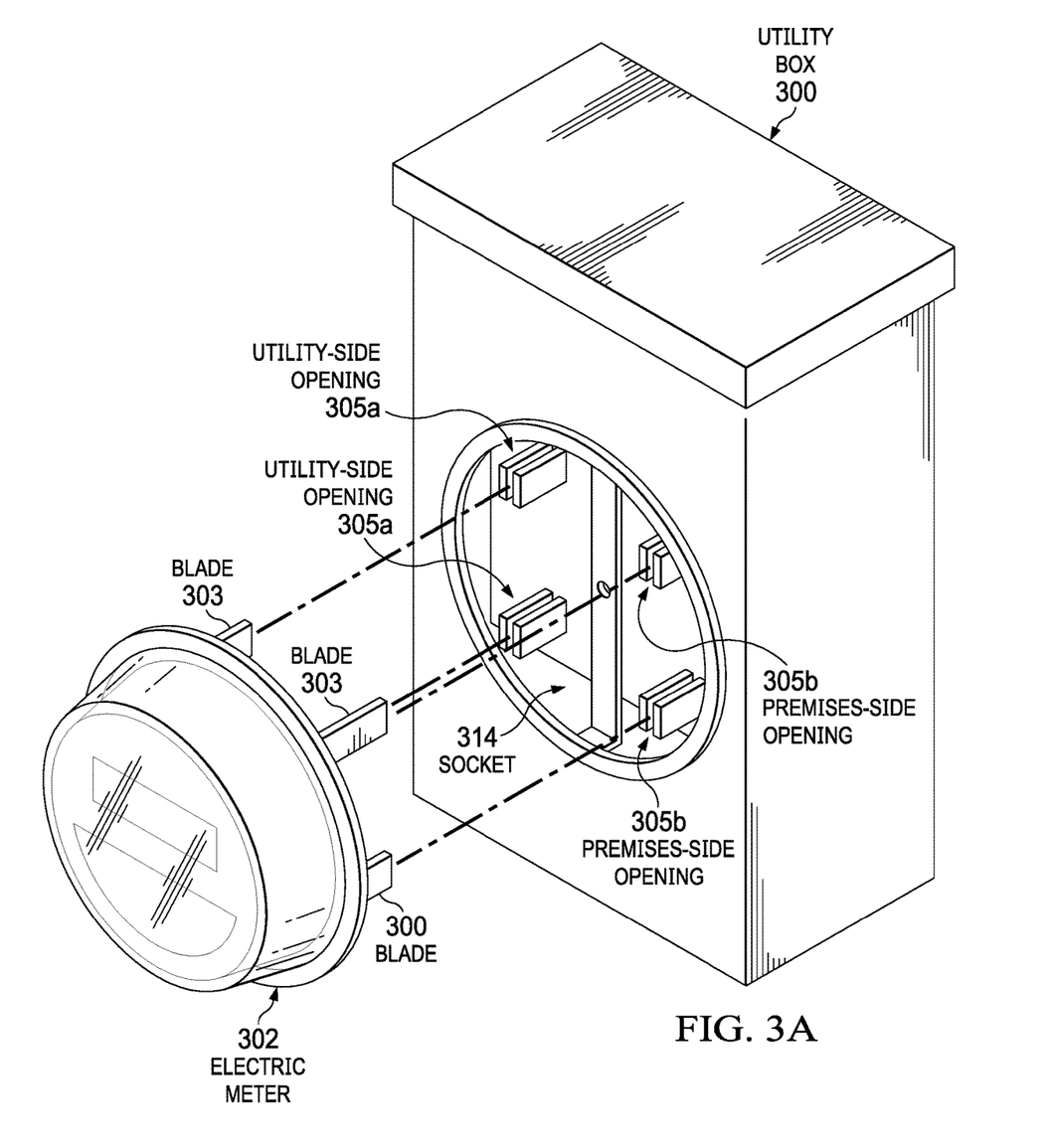
FIG. 3A shows an electric meter having blades inserted into openings of a meter socket accessible from the utility box.
Figure 3B:
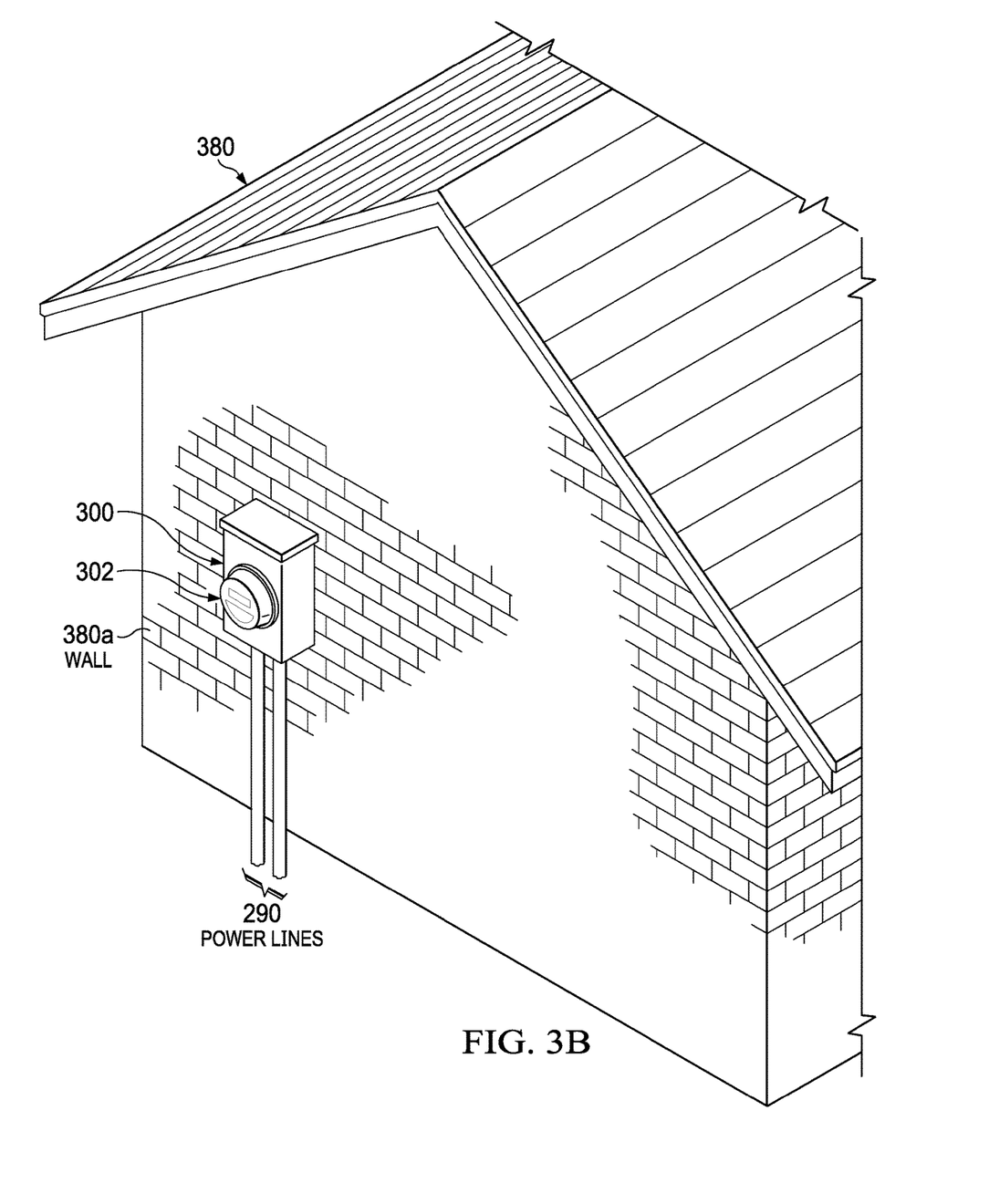
FIG. 3B shows the utility box including the electric meter installed on a wall of a premises.

FIG. 2B is a block diagram system portion representation 270 of a disclosed electric meter 252 including a gas sensor 218 mounted on the inside surface of the front wall of the meter shell 203 and extending out beyond the meter shell 203 that is configured to implement a disclosed method of detecting arcs generated by an electric meter 202, according to an example aspect. Because the gas sensor extends out beyond the meter shell 203, no vent holes in the meter shell 203 are generally needed FIG. 3A shows an electric meter 302 having blades 303 configured for insertion into openings shown as utility-side openings 305a and premises-side openings 305b of its meter socket 304, and FIG. 3B shows the electric meter 302 installed on a wall 380a of a premises 380. The utility box is shown as 300. The openings 305a and 305b are sized and configured so that the blades 303 may be positioned therein. The electric meter 302 may be fitted into the meter socket 304, as indicated by the dotted lines shown in FIG. 3A, such that the blades 303 are positioned in the openings 305a, 305b. Positioning the blades 303 within the openings 305a, 305b electrically connects the electrical meter 302 to the meter socket 304.

The blades 303 and the utility-side openings 305a can be configured such that electrical signals are transmitted between a utility-side of the meter socket 304 and the electrical meter 302, and the premises-side openings 305b are configured such that electrical signals are coupled between the electrical meter 302 and a premises-side of the meter socket 304. The electrical meter 302 can be configured such that disconnect circuitry (such as disconnect circuitry 222 described above) allows the electrical signals to be transmitted between the utility-side and the premises-side. For example, the disconnect circuitry 222 may be configured such that triggering the actuator 226 may interrupt the transmission of the electrical signals between the utility-side and the premises-side responsive to an arc being sensed, such as by interrupting the transmission of electrical signals between the blades 303 on the utility-side and the blades 303 on the premises-side of the electric meter 302.

While various disclosed aspects have been described above, it should be understood that they have been presented by way of example only, and not limitation. Numerous changes to the subject matter disclosed herein can be made in accordance with this Disclosure without departing from the spirit or scope of this Disclosure. For example, disclosed aspects can also be applied to gas meters or water meters which can experience arcing between components on their PCB. In addition, while a particular feature may have been disclosed with respect to only one of several implementations, such feature may be combined with one or more other features of the other implementations as may be desired and advantageous for any given or particular application.

The invention claimed is:

1. A method, comprising: providing at least one gas sensor positioned in a location proximate to blades of an electric meter that includes a meter shell in an outer utility box for sensing at least one gaseous compound product resulting from an arc discharge across air involving the blades, where the blades are configured to be within openings comprising utility-side openings and premises-side openings of a meter socket, and wherein the electric meter comprises a meter processor coupled to measurement circuitry and to a communications unit comprising a transceiver;

during operation of the electric meter, the gas sensor sensing a presence of the gaseous compound product; wherein responsive to the sensing of the gaseous compound product the gas sensor generates an output signal;

responsive to the output signal being determined to be above a predetermined threshold level, the electric meter sending an alert signal to an advanced metering infrastructure (AMI) which indicates an identity of the electric meter and that the electric meter had experienced the arc discharge;

wherein the gaseous compound molecules include nitric oxide (NO), nitrogen dioxide (NO2) and ozone (O3);

a separate sensor for the sensing of each of nitric oxide (NO), nitrogen dioxide (NO2) and ozone (O3);

the gas sensor of detecting NO2 is an electrochemical type sensor configured as a gas sensor module which has a selectable measurement range including 0 to 5 parts per million (ppm), 0 to 50 ppm, 0 to 100 ppm, or 0 to 1,000 ppm.

2. The method of claim 1, wherein the communications unit is coupled to an antenna, and wherein the alert signal comprises a wireless signal.

3. The method of claim 1, wherein the alert signal comprises a powerline communications signal.

4. The method of claim 1, wherein the AMI includes a central system for an electric utility associated with the electric meter, and wherein the AMI responsive to the alert signal, sends a disconnect signal to the electric meter.

5. The method of claim 1, wherein the at least one gas sensor protrudes in part outside the meter shell.

6. The method of claim 1, wherein the at least one gas sensor is located within the meter shell, and wherein there are ventilation holes in the meter shell.

7. The method of claim 1, wherein the at least one gas sensor comprises a first gas sensor for sensing a first gaseous compound product and a second gas sensor for sensing a second gaseous compound product.

8. An electric meter, comprising: a meter shell configured to be within an outer utility box; a meter socket and blades for electrically coupling to openings of the meter socket, the openings comprising utility-side openings and premises-side openings, wherein the blades protrude from and extend within the openings;

a meter processor coupled to measurement circuitry, and to a communications unit comprising a transceiver;

at least one gas sensor positioned in a location proximate to the blades for sensing at least one gaseous compound product resulting from an arc discharge across air involving the blades, wherein during operation of the electric meter, responsive to the gas sensor sensing a presence of the gaseous compound product, the gas sensor generates an output signal, and responsive to the output signal being determined to be above a predetermined threshold level, the electric meter triggering an alert signal to be transmitted to an advanced metering infrastructure (AMI) which indicates an identity of the electric meter and that the electric meter had experienced the arc discharge;

wherein the gaseous compound molecules include nitric oxide (NO), nitrogen dioxide (NO2) and ozone (O3);

a separate sensor for the sensing of each of nitric oxide (NO), nitrogen dioxide (NO2) and ozone (O3);

the gas sensor of detecting NO2 is an electrochemical type sensor configured as a gas sensor module which has a selectable measurement range including 0 to 5 parts per million (ppm), 0 to 50 ppm, 0 to 100 ppm, or 0 to 1,000 ppm.

9. The electric meter of claim 8, wherein the communications unit is coupled to an antenna, and wherein the alert signal comprises a wireless signal.

10. The electric meter of claim 8, wherein the alert signal comprises a powerline communications signal.

11. The electric meter of claim 8, wherein the at least one gas sensor protrudes in part outside the meter shell.

12. The electric meter of claim 8, wherein the at least one gas sensor is located within the meter shell, and wherein there are ventilation holes in the meter shell.

13. The electric meter of claim 8, wherein the at least one gas sensor comprises a first gas sensor for sensing a first gaseous compound product and a second gas sensor for sensing a second gaseous compound product.

* * * * *